United States Patent [19]

McKinnie et al.

[11] Patent Number: 4,533,753

[45] Date of Patent: * Aug. 6, 1985

[54] (HYDROCARBYLTHIO)PHENOLS AND THEIR PREPARATION

[75] Inventors: Bonnie G. McKinnie; Paul F. Ranken, both of Baton Rouge, La.

[73] Assignee: Ethyl Corporation, Richmond, Va.

[*] Notice: The portion of the term of this patent subsequent to Apr. 13, 1999 has been disclaimed.

[21] Appl. No.: 484,338

[22] Filed: Apr. 12, 1983

Related U.S. Application Data

[63] Continuation-in-part of Ser. No. 430,553, Sep. 30, 1982, now Re. 31,771.

[51] Int. Cl.$^3$ .................. C07C 148/00; C07C 149/36
[52] U.S. Cl. ........................ 568/47; 568/54; 252/45
[58] Field of Search ............ 568/47, 54; 252/45

[56] References Cited

U.S. PATENT DOCUMENTS

| 2,259,861 | 10/1941 | Richardson | 568/54 X |
| 2,745,878 | 5/1956 | Mavity | 568/54 |
| 2,831,898 | 4/1958 | Ecke et al. | 260/624 |
| 2,923,743 | 2/1960 | Delfs et al. | 568/54 |
| 2,923,745 | 2/1960 | Buls et al. | 260/624 |
| 3,134,818 | 5/1964 | Farah et al. | 568/54 |
| 3,149,139 | 9/1964 | Meisert | 568/54 X |
| 3,200,157 | 8/1965 | Buls et al. | 260/624 |
| 3,246,040 | 4/1966 | Reifschneider | 568/54 X |
| 3,335,190 | 8/1967 | Du Bois et al. | 568/54 |
| 3,629,225 | 12/1971 | Allphin, Jr. | 252/45 X |
| 3,714,264 | 1/1973 | Spacht | 568/54 |
| 3,728,399 | 4/1973 | Spacht | 568/47 |
| 4,120,866 | 10/1978 | Winkler | 568/54 X |
| 4,128,530 | 10/1978 | Cottman | 568/54 X |
| 4,324,920 | 4/1982 | McKinnie et al. | 568/54 |

FOREIGN PATENT DOCUMENTS

| 2055770 | 11/1970 | Fed. Rep. of Germany | 568/54 |
| 0953834 | 4/1964 | United Kingdom | 568/54 |

OTHER PUBLICATIONS

Farah et al., J. Organic Chem., vol. 28, (1963), pp. 2807–2809, "Alkyl-Mercaptophenols by Sulfenylation of Phenols".
Pedersen, et al., Tetrahedron, vol. 26, (1970), pp. 4449–4457, "o-Hyroxyphenyl Alkyl Sulfides, Sulfoxides and Sulfones".
Cabiddu, et al., Gazetta Chimica Italiana, vol. 99, No. 4, pp. 397–410, (1969).
Trost et al., Chemical Abstracts, vol. 89, 197,093z, (1978).

*Primary Examiner*—Diana G. Rivers
*Attorney, Agent, or Firm*—Donald L. Johnson; John F. Sieberth; Patricia J. Hogan

[57] ABSTRACT (Hydrocarbylthio)phenols containing at least two hydrocarbylthio groups on a phenolic ring are prepared by reacting phenolic compounds with an excess of hydrocarbyl disulfide in the presence of catalytic amounts of an aluminum phenoxide. Novel and useful (hydrocarbylthio)phenols containing at least two hydrocarbylthio groups on a phenolic ring can be prepared by this process. (Hydrocarbylthio)phenols containing at least two hydrocarbylthio groups on a phenolic ring are effective antioxidants for organic material normally susceptible to oxidative deterioration, such as mineral oil.

24 Claims, No Drawings

(HYDROCARBYLTHIO)PHENOLS AND THEIR PREPARATION

REFERENCE TO RELATED APPLICATION

This application is a continuation-in-part of our co-pending reissue application Ser. No. 430,553, filed Sept. 30, 1982 now U.S. Pat. No. Re. 31,771.

INTRODUCTION

This invention relates to novel and useful (hydrocarbylthio)phenols containing at least two hydrocarbylthio groups and to a process for thier preparation.

BACKGROUND OF THE INVENTION

Ortho-(hydrocarbylthio)phenols are useful compounds, e.g., as intermediates in the preparation of hypotensive drugs and agricultural chemicals such as plant protection agents, herbicides, pesticides and the like. U.S. Pat. No. 2,923,743 describes a process for the production of aryl-alkyl thioethers by reacting a dialkyl disulfide with aromatic compounds such as phenol, chlorophenol, p-cresol, 2-naphthol, etc., in the presence of suitable condensation agents, such as for example, aluminum chloride, aluminum bromide, ferric chloride, zinc chloride, tin tetrachloride, antimony pentachloride, boron fluoride and bleaching earth. At Column 1, lines 31-36, that patent discloses:

"These condensation agents can be added in different amounts. In general there should be added at least molecular amounts referred to the dialkyl disulfide but there can be used also higher amounts e.g. a 3-fold surplus of the condensation agent."

U.S. Pat. No. 3,246,040 discloses the synthesis of certain substituted phenolic compounds containing two alkylthio groups and from 0 to 3 halo or nitro groups. This patent discloses that the compounds are useful as pesticides; as inhibitors of the germination of fungus spores, they are effective fungistats. They are also useful as intermediates in the preparation of biologically active materials such as organic phosphates.

In our U.S. Pat. No. 4,324,920, the disclosure of which is incorporated herein by reference, we disclose a process for the preparation of ortho-(hydrocarbylthio)phenols by contacting phenols, having at least one hydrogen on a carbon atom ortho to a hydroxy group, with hydrocarbyl disulfides in the presence of catalytic amounts of aluminum phenoxide.

SUMMARY OF THE INVENTION

It has been found that hydrocarbylthio-substituted phenols containing at least two hydrocarbylthio groups on a phenolic ring can be prepared in good yields by contacting phenols, having at least two positions available for substitution on a phenolic ring, with an excess of hydrocarbyl disulfides in the presence of catalytic amounts of aluminum phenoxide. An excess of hydrocarbyl disulfide is defined to be a quantity of hydrocarbyl disulfide greater than the stoichiometric amount required for the number of hydrocarbylthio groups desired in the (hydrocarbylthio)phenol. A catalytic amount of aluminum phenoxide means less than molecular or equivalent amounts of aluminum phenoxide. The process of this invention requires no solvent and makes use of cheap and available materials. Still further advantages will be apparent from the following disclosure.

It has also been found pursuant to this invention that novel and useful products can be produced by the foregoing process. Among the preferred compounds of the invention are compounds of Formula I:

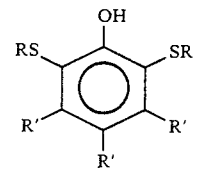

In Formula I, at least two of the R' groups are the same or different hydrocarbyl groups and the remaining R' group is hydrogen or hydrocarbyl.

A further group of preferred compounds of this invention are compounds of Formula II:

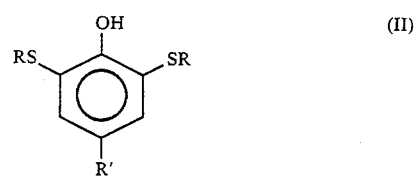

The R' group in Formula II is hydrogen or, more preferably, a hydrocarbyl group.

Another preferred group of compounds of this invention is depicted by Formula III:

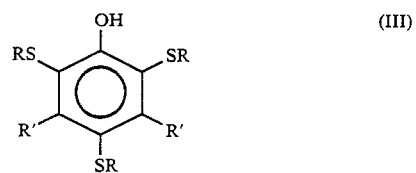

The R' groups in Formula III may be the same or different, and are hydrogen atoms or hydrocarbyl groups.

Still another group of preferred compounds of this invention are compounds of Formula IV:

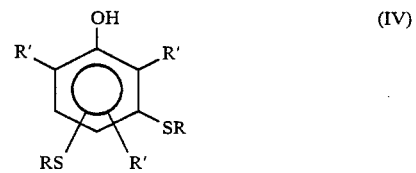

In Formula IV, the R' groups in the 2- and 6-positions are the same or different hydrocarbyl groups while the other R' group is a hydrogen atom or a hydrocarbyl group, which hydrocarbyl group can be the same as or different from the hydrocarbyl groups in the 2- and 6-positions. As indicated by Formula IV, either the 4- or 5-position is occupied by an —SR group and the other of these positions is occupied by an R' group.

Particularly preferred compounds within the scope of Formula IV are the compounds of Formula V:

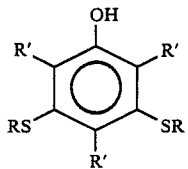

(V)

In Formula V, the R' groups in the 2- and 6-positions are the same or different hydrocarbyl groups while the R' group in the 4-position is a hydrogen atom or a hydrocarbyl group, which hydrocarbyl group can be the same as or different from the hydrocarbyl groups in the 2- and 6-positions.

Yet another class of preferred compounds of this invention are those of Formula VI:

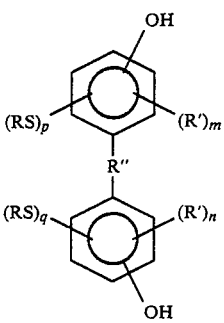

(VI)

The R' groups in Formula VI may be the same or different, and are hydrogen atoms or hydrocarbyl groups.

A particularly preferred subgroup of compounds within the ambit of Formula VI are compounds of Formula VII:

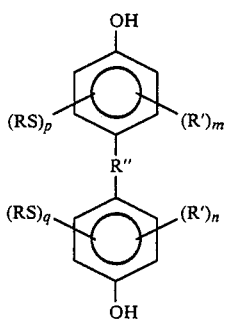

(VII)

The R' groups in Formula VII may be the same or different, and are hydrogen atoms or hydrocarbyl groups.

In the above respective Formulas (I–VII), the R groups are hydrocarbyl groups which may differ but which preferably are the same in any given compound. R may be, for example, an alkyl group or a cycloalkyl group typically having up to about 10 carbon atoms, such as methyl, ethyl, propyl, n-butyl, sec-butyl, tert-butyl, hexyl, octyl, decyl, cyclopropyl, cyclopentyl, cyclohexyl, cycloheptyl, cyclooctyl, cyclopropylcarbinyl, and the like. Preferably R is an alkyl group containing up to about 4 carbon atoms, most preferably methyl or ethyl.

The R' hydrocarbyl groups of Formulas I–VII are either saturated aliphatic or cycloaliphatic groups or are aromatic groups. In most cases they will be: alkyl of 1 to 50 carbon atoms; cycloalkyl of from 3 to 20 carbon atoms; aryl of from 6 to 12 carbon atoms; alkaryl of from 7 to 20 carbon atoms; and aralkyl of from 7 to 20 carbon atoms. However, in Formula II the alkyl group may contain as many as 700 or more carbon atoms.

R'' in Formulas VI and VII is an alkylidene or an alkylene group of from 1 to about 10 carbon atoms. Alternatively, R'' is a direct carbon-to-carbon linkage connecting the two phenolic rings together. Other linking groups, R'', include an oxygen atom, a sulfur atom, and such groups as

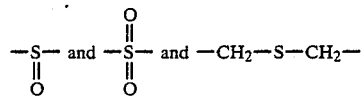

and the like.

In Formulas VI and VII, m and n are integers from 0 to 4 (both inclusive), p and q are integers from 0 to 4 (both inclusive) and either or both of p and q is an integer of at least 2. The total of m and p and the total of n and q are each 4.

Another aspect of this invention involves the discovery that the compounds of this invention are effective antioxidants. Tests have shown that various compounds of this invention are highly effective as antioxidants in lubricating oil and these results indicate that the compounds of this invention will exhibit antioxidant properties in a variety of substrates normally susceptible to oxidative deterioration on prolonged exposure to air or oxygen.

Thus, in another of its embodiments this invention further provides an organic material or substrate that is normally susceptible to oxidative deterioration, which contains a (hydrocarbylthio)phenol having at least two hydrocarbylthio groups on a phenolic ring, such (hydrocarbylthio)phenol being present in a small amount sufficient to inhibit such deterioration.

DETAILED DESCRIPTION OF THE INVENTION

Process

In accordance with one aspect of this invention there is provided a process for the preparation of hydrocarbylthio-substituted phenols containing at least two hydrocarbylthio groups on a phenolic ring which comprises contacting (i.e., reacting) phenols, having at least two positions available for substitution on a phenolic ring, with an excess of a hydrocarbyl disulfide in the presence of an aluminum phenoxide catalyst, the molar ratio of the catalyst to the disulfide being less than 1, preferably between about 0.002 and 0.3 and most preferably between about 0.01 and 0.1. The process is normally conducted at a temperature within the range of from about 0° C. to about 300° C. at which the desired reaction takes place. Preferably the process is performed at a temperature of from about 100° C. to about 300° C. and most preferably from about 100° C. to about 200° C. With the process of this invention one mole of hydrocarbylthiol (RSH) is formed as by-product for each hydrocarbylthio group (RS—) substituted onto the phenol. Without being bound to a particular mechanism or theory, it appears that the reacting hydrocarbyl disulfide is split into two species or moieties, one being substituted onto the phenol the other forming the corresponding hydrocarbylthiol by-product. In a particularly preferred embodiment, the process of this invention is conducted in such a way that the hydrocarbylthiol by-product is removed from the reaction vessel essentially as rapidly as it is formed. This can be accomplished for example by conducting the reaction at reflux temperature and/or under reduced pressures (i.e. below atmospheric pressure) and/or under a sweep of an inert gas so that the hydrocarbylthiol by-product evolved is rapidly removed or purged from the reaction vessel. Alternatively, the reaction may be carried out at pressures greater than one atmosphere with the hydrocarbylthiol by-product being removed by distillation.

In still another preferred embodiment of this invention the hydrocarbyl disulfide reactant is a saturated aliphatic or cycloaliphatic hydrocarbyl disulfide, most preferably a lower alkyl disulfide.

The aluminum phenoxide catalyst used in the practice of this invention can be formed in various ways. For example it can be formed by contacting aluminum metal, preferably in the form of turnings, powders, particles and the like, with the phenol at elevated temperatures (e.g. 100°–200° C.) until cessation of hydrogen evolution. Another way of forming the catalyst used in this invention is by simply contacting an aluminum alkyl such as triethylaluminum with the phenol. Still another method of forming the catalyst used herein involves contacting aluminum chloride (i.e. $AlCl_3$) and the phenol at elevated temperatures, e.g. between 100° and 200° C., and purging the system of the hydrogen chloride generated during the preparation of the phenoxide catalyst. The source of the aluminum phenoxide catalyst does not materially affect the reaction and other methods known in the art for the formation of these compounds can be successfully employed herein. Exemplary methods for preparing aluminum phenoxide catalysts useful in the process of this invention appear in U.S. Pat. Nos. 2,831,898, 2,923,745 and 3,200,157. The preferred catalyst is aluminum triphenoxide, although a diphenoxide catalyst, e.g., diphenoxyaluminum chloride (which may be formed in the reaction of aluminum chloride and phenol) or diphenoxyaluminum hydroxide (which may be formed by reaction of aluminum chloride and phenol containing small amounts of water), can also be used in the practice of this invention.

Hydrocarbyl disulfides which may be employed in the practice of this invention include the alkyl disulfides and the cycloalkyl disulfides, these respective disulfides preferably having up to about 10 carbon atoms in each alkyl or cycloalkyl group. Preferably the hydrocarbyl disulfide is a lower alkyl disulfide, i.e., an alkyl disulfide in which each alkyl group contains 1 to about 6 carbon atoms, such as, for example, methyl disulfide and ethyl disulfide, these two compounds being particularly preferred reactants because of their availability and good reactivity in the process. Aromatic disulfides, unsaturated aliphatic disulfides, unsaturated cycloaliphatic disulfides, as well as substituted hydrocarbyl disulfides, may be used provided they do not interfere with the reaction. However, if the final product is to be used as an antioxidant in lubricating oils, it is preferred that the product be essentially halogen-free. Hydrocarbyl disulfides which may be used herein include, for example, methyl disulfide, ethyl disulfide, methyl ethyl disulfide, n-butyl disulfide, sec-butyl disulfide, tert-butyl disulfide, propyl disulfide, cyclopentyl disulfide, cyclohexyl disulfide, cycloheptyl disulfide and the like. When it is desired to introduce two different —SR groups into the product, two different hydrocarbyl disulfides will normally be employed in the reaction, either simultaneously or consecutively. The total quantity of the two disulfides used will be in excess of the stoichiometric amount required to introduce the number of —SR groups desired in the product.

Phenols used herein can be mono- or poly-nuclear, e.g. the naphthols. The phenols can contain substituents as long as they do not interfere with the reaction, and as long as there are at least two positions available for substitution on a phenolic ring by hydrocarbylthio groups. The aryl portion of the hydroxy aromatic compound may be linked to or fused with other cyclic systems including heterocyclic systems such as those containing oxygen, nitrogen and/or sulfur atoms in the rings. Examples of the aryl portion of the hydroxy aromatic compound include but are not limited to the following: benzene, biphenyl, 2,2-diphenylpropane, 1,3-dimethylbenzene, 1,2,3-trimethylbenzene, naphthalene, anthracene, phenanthrene, indene, benzofuran, thionaphthene, 1,2-benzopyran, 1,4-benzopyran, quinoline, isoquinoline, acenaphthene, fluorene, dibenzopyrrole, xanthene, thianthrene, naphthacene, chrysene, pyrene, triphenylene, biphenyl, and the like. In the phenolic derivatives of these compounds the hydroxy group is of course bonded to a nuclear carbon atom of a benzene ring.

Substituents which can be present in the hydroxy aromatic compounds should be relatively inert under the conditions of the reaction. For example, any of the previously mentioned aromatics may be substituted in a variety of positions with alkyl, aryl, aralkyl, alkaryl and cycloalkyl radicals, chlorine, fluorine, alkoxy, and the like. Desirably, the phenolic reactant does not contain bromine or iodine substituents as these appear to interfere with the desired reaction. If the final product is to be used as an antioxidant in lubricating oils, it is preferred that the product be formed from a phenolic compound that is essentially halogen-free. A few representative examples of these substituted phenols that may be used in the process of this invention include but are not limited to: 4-chlorophenol, 4-(4-chlorophenyl)phenol, p-cresol, 4-phenylphenol, 4-benzylphenol, 4-phenoxyphenol, and the like.

Those skilled in the art will appreciate that factors of steric hindrance and the relative position of the substituent(s) on the ring should be taken into account when determining what substituents may be present in the starting phenolic compound. Also, since some tertiary aliphatic groups ortho to an aromatic hydroxy group may undergo dealkylation, aliphatic groups in the ortho position(s) are preferably secondary aliphatic groups, and most preferably are primary aliphatic groups.

A preferred class of phenolic reactants are those which can be represented by Formula VIII:

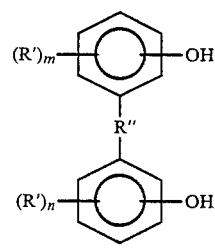

(VIII)

Another preferred class of phenolic reactants for use in the process are those which can be presented by Formula IX:

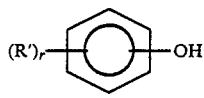

In Formulas VIII and IX, the R' groups are the same or different hydrocarbyl groups. Typically, each R' hydrocarbyl group will be essentially devoid of olefinic and acetylenic unsaturation and usually will contain no more than about 50 carbon atoms. Thus, the R' groups may be an alkyl group having from 1 to about 50 or more (and preferably from 1 to about 20) carbon atoms, such as, for example, methyl, ethyl, propyl, isopropyl, tert-butyl, pentyl, heptyl, eicosyl, triacontyl, pentacontyl and the like; an aryl group having from 6 to about 12 carbon atoms, such as, for example, phenyl, 4-biphenylyl, 1-naphthyl, and the like; an aralkyl group having from about 7 to about 20 carbon atoms, such as, for example, benzyl, phenylethyl(phenethyl), phenylhexyl, phenylheptyl, phenyloctyl, phenylnonyl, phenylundecyl, phenyldodecyl, phenyltridecyl, phenyltetradecyl, phenylcyclopropyl, phenylcyclohexyl, 2,4-dimethylbenzyl, and the like; an alkaryl group having from about 7 to about 20 carbon atoms, such as, for example, tolyl, xylyl, mesityl, butylphenyl, iso-butylphenyl, sec-butylphenyl, tert-butylphenyl, ethylphenyl, pentylphenyl, 4-methylbiphenyl, 3-methylbiphenyl and the like; and a cycloalkyl group having from 3 to about 20 carbon atoms, such as, for example, cyclopropyl, cyclohexyl, cyclooctyl, bicyclohexyl, butylcyclohexyl, methylcyclohexyl, cyclobutyl, cyclodecyl, cyclododecyl, cyclohexylphenyl, cyclopentyl, and the like, as well as other hydrocarbyl groups exemplified by cyclopropylphenyl, α-cyclopropylphenylmethyl and the like. However, long chain monoalkyl phenols (usually the 4-alkyl isomer) made by alkylating phenol with propylene oligomers or isobutylene oligomers of molecular weights as high as 10,000 may be used. Of these long chain monoalkyl phenols, 4-alkylphenols in which the alkyl group has from about 50 to about 700 carbon atoms are preferred.

In Formula VIII, m and n are integers of from 0 to 4 (both inclusive) with the understanding that there will be at least one phenolic ring with at least two positions available for substitution by hydrocarbylthio groups.

In Formula VIII, R'' is either a direct carbon-to-carbon bond directly linking the two phenolic rings together, or is a suitable divalent linking group such as alkylidene, alkylene, an oxygen atom (ether linkage), a sulfur atom, a group such as

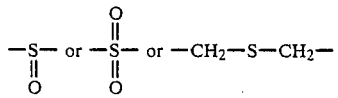

and the like. Preferably R'' is an alkylidene or an alkylene group of from 1 to about 10 carbon atoms, such as, for example, methylidene, ethylidene, propylidene, isopropylidene, butylidene, hexylidene, decylidene, methylene, ethylene, propylene, isopropylene, butylene, hexylene, decylene, and the like. Preferably the alkylidene or alkylene group has up to about 4 carbon atoms. In the most preferred compounds of Formula VIII, R'' is either isopropylidene or methylene.

In Formula IX, r is an integer of from 0 to 3, and preferably from 0 to 2 (both inclusive).

Some examples of the phenolic compounds represented by Formulas VIII and IX include but are not limited to: phenol, p-cresol, a mixture of o- and p-cresols, m-cresol, a mixture of 2- and 4-isomers of nonylphenol, 4-tert-butylphenol, 4-phenylphenol, 2,2'-diphenol, 4-(1,1,3,3-tetramethylbutyl)phenol, 3,5-dimethylphenol, a mixture of o-, m-, and p-cresols, 4-pentacontylphenol, 2-cyclohexylphenol, 4-cyclooctylphenol, 4-(2,4-dimethylcyclohexyl)phenol, 2,6-dimethylphenol, 2,5-dimethylphenol, 3,4-dimethylphenol, 3,4,5-trimethylphenol, 4-(2-eicosyl)phenol, 4-(4-tridecylbenzyl)phenol, 4,4'-diphenol, 4-(3,5-di-sec-heptylphenyl)phenol, 2-sec-butylphenol, 2-ethylphenol, 2,6-diethylphenol, 2-(α-methylbenzyl)phenol, 2-cyclopentylphenol, a mixture of isomeric o-sec-pentacontylphenols, 4-tert-amylphenol, 4-(α-methyl-4-dodecylbenzyl)phenol, 2-phenylphenol, 2-(4-tetradecylphenyl)phenol, 2-triacontylphenol, 2-isopropylphenol, 2-(α-methyl-4-sec-amylbenzyl)phenol, 4,4'-isopropylidenediphenol(bisphenol A), 4,4'-methylenebisphenol, 2,2'-methylenebisphenol, 4,4'-methylenebis(2-ethylphenol), 4,4'-propylidenebisphenol, 4,4'-butylidenebis(phenol), 2,2'-ethylidenebisphenol, 4,4'-pentylidenebisphenol, 1-naphthol, 2-naphthol, 2-ethoxyphenol, 3-ethoxyphenol, 4-ethoxyphenol, 4-octyloxyphenol, 4-hexacosylphenol, 4-triacontylphenol, 4-tetracontylphenol, and the like.

A particularly preferred embodiment of this invention involves reaction of (i) a phenol of Formula VIII above wherein m and n are both zero and R'' is an alkylidene group or alkylene group containing up to 4 carbon atoms, a direct carbon-to-carbon bond linking the two phenolic rings together, or an oxygen atom, with (ii) a lower alkyl disulfide, i.e., each alkyl group has from 1 to about 6 carbon atoms, using an aluminum phenoxide catalyst in the manner described above. Another particularly preferred embodiment involves conducting this reaction using a phenol of Formula IX above wherein r is an integer from zero to 1 (both inclusive) and R' is a hydrocarbyl group essentially devoid of olefinic and acetylenic unsaturation and containing up to about 50 carbon atoms. In a further particularly preferred embodiment, the phenol used is a monoalkylphenol in which the alkyl group has from about 50 to about 700 or more carbon-atoms. Still another particularly preferred embodiment involves conducting this reaction with a phenol of Formula IX above wherein r is 2 and each R' is a hydrocarbyl group essentially devoid of olefinic and acetylenic unsaturation and containing up to about 30 carbon atoms. It is especially desirable to perform these embodiments under conditions whereby the alkyl mercaptan by-product is removed from the reaction mixture during the course of the reaction.

Those skilled in the art will recognize that phenolic compounds having one or more of the ortho/para positions already occupied by substituent groups may be utilized in the process of this invention, providing the presence of those substituent groups still permit the phenolic compound to be substituted by at least two hydrocarbylthio groups. Generally speaking, however, it is preferable, in terms of ease of reaction, to use phenolic compounds whereby one or more of the positions available for substitution by hydrocarbylthio groups are selected from amongst the ortho and para positions.

In practicing the process of this invention the hydrocarbyl disulfide is normally added to the phenol-aluminum phenoxide mixture although the order of addition is not critical. Once the phenol and hydrocarbyl disulfide have been contacted in the presence of the catalyst the reaction is allowed to proceed at temperatures and times which can vary depending upon such considerations as the boiling point of the hydrocarbylthiol generated during reaction, the percent yield of product desired, the melting point of the reactants and the like. In general, when the reaction is carried out at atmospheric pressure, temperatures slightly above the boiling point of the hydrocarbyl disulfide are employed. In a particularly preferred aspect, the mixture is maintained at or near its reflux temperature. Of course if pressures below atmospheric pressure are employed the corresponding temperature may also be decreased. In a preferred embodiment as much of the hydrocarbylthio by-product as is feasible is removed, e.g. by vacuum distillation and the like. Total reaction times of more than one day are typically employed when the reaction is run at atmospheric pressure. However, if desired, the reaction may be conducted at pressures greater than atmospheric pressure with provision being made for removal of the alkyl mercaptan by-product and thereby shorter reaction times may be employed.

In practicing this invention a broad range of proportions of reactants can be utilized. That is, the relative molar amounts of phenol to the disulfide can vary widely; however, the relative proportions employed normally fall within the range of from about 1:2.1 to about 1:20, and most preferably within the range of from about 1:2.5 to about 1:6. Furthermore, while the process of this invention can be carried out without the use of solvents or diluents they may nevertheless be used, if desired, so long as they are inert to the reaction disclosed herein. Hydrocarbons and ethers are illustrative of the solvents that may be employed. The process is preferably carried out under substantially anhydrous conditions, but conditions wherein trace or small amounts of water are present can be used. Accordingly, an inert atmosphere is normally employed in the present process.

Compounds

As noted above, another aspect of this invention involves the provision of novel and useful compounds producible by the process described above. These compounds are depicted hereinabove in Formulas I through VII.

Illustrative examples of compounds which are provided in accordance with this invention include but are not limited to such compounds as the following:

Formula I 3,5-dimethyl-2,6-bis(methylthio)phenol,
3,4,5-trimethyl-2,6-bis(methylthio)phenol,
3,4-dimethyl-2,6-bis(methylthio)phenol,
3,5-dimethyl-2,6-bis(ethylthio)phenol,
3,4-dimethyl-2,6-bis(propylthio)phenol,
3-ethyl-5-methyl-2,6-bis(methylthio)phenol, and
3,5-diethyl-2,6-bis(butylthio)phenol.

Formula II 2,6-bis(methylthio)phenol,
2,6-bis(ethylthio)phenol,
2,6-bis(nonylthio)phenol,
2,6-bis(cyclopentylthio)phenol,
4-methyl-2,6-bis(methylthio)phenol,
4-methyl-2,6-bis(butylthio)phenol,
4-methyl-2,6-bis(decylthio)phenol,
4-methyl-2,6-bis(cyclohexylthio)phenol,
4-ethyl-2,6-bis(methylthio)phenol,
4-butyl-2,6-bis(ethylthio)phenol,
4-tert-butyl-2,6-bis(methylthio)phenol,
4-tert-butyl-2,6-bis(propylthio)phenol,
4-tert-amyl-2,6-bis(methylthio)phenol,
4-(1,1,3,3-tetramethylbutyl)-2,6-bis(methylthio)phenol,
4-(1,1,3,3-tetramethylbutyl)-2,6-bis(ethylthio)phenol,
4-(1,1,3,3-tetramethylbutyl)-2,6-bis(decylthio)phenol,
4-nonyl-2,6-bis(methylthio)phenol,
4-eicosyl-2,6-bis(ethylthio)phenol,
4-pentacontyl-2,6-bis(methylthio)phenol,
4-cyclohexyl-2,6-bis(methylthio)phenol,
4-phenyl-2,6-bis(methylthio)phenol,
4-(p-tolyl)-2,6-bis(ethylthio)phenol, and
4-biphenylyl-2,6-bis(methylthio)phenol.

Formula III 2,4,6-tris(methylthio)phenol,
2,4,6-tris(ethylthio)phenol,
2,4,6-tris(propylthio)phenol,
2,4,6-tris(decylthio)phenol,
3-methyl-2,4,6-tris(methylthio)phenol,
3-methyl-2,4,6-tris(ethylthio)phenol,
3,5-dimethyl-2,4,6-tris(methylthio)phenol,
3,5-dimethyl-2,4,6-tris(ethylthio)phenol, and
3-ethyl-5-methyl-2,4,6-tris(methylthio)phenol.

Formula IV 2,6-dimethyl-3,4-bis(methylthio)phenol,
2,6-dimethyl-3,4-bis(ethylthio)phenol.
2,6-dimethyl-3,4-bis(octylthio)phenol,
2,6-diethyl-3,4-bis(methylthio)phenol, and
2-ethyl-6-isopropyl-3,4-bis(methylthio)phenol.

Formula V 2,6-dimethyl-3,5-bis(methylthio)phenol,
2,6-dimethyl-3,5-bis(ethylthio)phenol,
2-ethyl-6-methyl-3,5-bis(methylthio)phenol,
2,6-diethyl-3,5-bis(methylthio)phenol,
2,4,6-trimethyl-3,5-bis(methylthio)phenol,
2,4,6-trimethyl-3,5-bis(ethylthio)phenol, and
2-ethyl-4,6-dimethyl-3,5-bis(methylthio)phenol.

Formula VI 2,2'-methylenebis[4,6-bis(methylthio)phenol],
2,2'-methylenebis[4,6-bis(hexylthio)phenol],
4,4',6,6'-tetra(methylthio)-2,2'-ethylidenediphenol,
4,4',6-tris(methylthio)-2,2'-isopropylidinediphenol,
4,4',6,6'-tetra(ethylthio)-2,2'-butylidenediphenol.
4,4',6-tris(ethylthio)-2,2'-butylidenediphenol,
2',4,6,6'-tetra(methylthio)-2,4'-diphenol,
2,2'-bis[4,6-bis(methylthio)phenol], and
2,2'-bis[4,6-bis(ethylthio)phenol].

Formula VII 2,2',6,6'-tetra(methylthio)-4,4'-isopropylidenediphenol,
2,2',6,6'-tetra(ethylthio)-4,4'-isopropylidenediphenol,
2,2',6,6'-tetra(propylthio)-4,4'-isopropylidenediphenol,
2,2',6,6'-tetra(butylthio)-4,4'-isopropylidenediphenol,
3,3'-dimethyl-2,2',6,6'-tetra(methylthio)-4,4'-isopropylidenediphenol, 3,3'-diethyl-2,2',6,6'-tetra(ethylthio)-4,4'-isopropylidenediphenol,
2,2',6-tris(methylthio)-4,4'-isopropylidenediphenol,
2,2',6-tris(ethylthio)-4,4'-isopropylidenediphenol,
2,2',6-tris(propylthio)-4,4'-isopropylidenediphenol,
2,2',6-tris(butylthio)-4,4'-isopropylidenediphenol,
3,3'-dimethyl-2,2',6-tris(methylthio)-4,4'-isopropylidenediphenol,
3,3'-diethyl-2,2',6-tris(ethylthio)-4,4'-isopropylidenediphenol,
4,4'-methylenebis[2,6-bis(methylthio)phenol],
4,4'-methylenebis[2,6-bis(ethylthio)phenol],
4,4'-methylenebis[2,6-bis(propylthio)phenol],
4,4'-methylenebis[2,6-bis(butylthio)phenol],
2,2',6,6'-tetra(methylthio)-4,4'-ethylidenediphenol,
2,2',6,6'-tetra(ethylthio)-4,4'-ethylidenediphenol,
2,2',6,6'-tetra(methylthio)diphenol,
2,2',6,6'-tetra(ethylthio)diphenol,
2,2',6,6'-tetra(propylthio)diphenol,
2,2',6,6'-tetra(butylthio)diphenol,
2,2',6-tris(methylthio)diphenol,
2,2',6-tris(ethylthio)diphenol,
3,3'-dimethyl-2,2',6,6'-tetra(propylthio)diphenol,
3,3',5-tris(methylthio)-4,4'-dihydroxydiphenylether, and
3,3',5,5'-tetra(methylthio)-4,4'-dihydroxydiphenylether.

Still other compounds which may be produced by the process described hereinabove include such compounds as:
6-nonyl-2,4-bis(methylthio)phenol,
2,4-bis(ethylthio)phenol,
3,5-dimethyl-2,4-bis(methylthio)phenol
2-methyl-4,6-bis(ethylthio)phenol,
6-methyl-2,4-bis(methylthio)phenol,
2,4-bis(butylthio)phenol,
3,5-dimethyl-2,4-bis(ethylthio)phenol, and the like.

Of interest is the production by the process of this invention of compounds of Formulas IV and V wherein the phenolic compound is substituted by a hydrocarbylthio group in either or both of the meta positions relative to the hydroxyl group. Reference to processes giving direct meta-substitution of phenols is rarely encountered in the scientific literature, especially where the para position carries a hydrogen atom.

The preparation of the compounds of this invention will be still further apparent from the following illustrative examples which are not intended to limit the invention in any manner.

In Examples 1–10 reactions were carried out under nitrogen in a 3-neck round bottom flask equipped with a magnetic stirring bar, thermometer, and a Vigreux column. On top of the Vigreux column was a reflux condenser.

Also, unless noted otherwise, distillations were performed using a 7-cm Vigreux column.

Further, VPC analyses were performed on either a 15 foot OV-25 (8%) or a 10 foot OV-101 (6%) column programmed from 100° C. to 280° C. at 10° C. per minute, unless noted otherwise.

EXAMPLE 1

Preparation of 4-Methyl-2,6-bis(methylthio)phenol

A mixture of 10.8 g (0.10 mole) of p-cresol and 10 ml of cyclohexane was ditilled free of cyclohexane to remove water. Aluminum (about 10–20 mesh), 0.135 g (5.0 mmole), was then added to the p-cresol and the mixture was heated at 150°–170° C. until all the metal dissolved. The mixture was cooled and 10 ml of xylene and 22.5 ml (0.25 mole) of methyl disulfide were added. This mixtue was refluxed.

After a total of 6 days at reflux the mixture was dilued with THF, extracted with 6N HCl and then saturated NaCl, and dried over Na2SO4. Distillation gave 13.06 g (65% yield) of a product which was a clear liquid having a b.p. of 108°–111° C. at 0.1 mm. NMR analysis showed the product to be 4-methyl-2,6-bis(methylthio)phenol.

EXAMPLE 2

Preparation of 4-Tert-butyl-2,6-bis(methylthio)phenol

A mixture of 30.0 g (0.20 mole) of 4-tert-butylphenol and 0.34 g (0.013 mole) of aluminum (10–20 mesh) was heated to 190° C. No reaction was observed so the mixture was cooled and 0.20 ml (0.0015 mole) triethylaluminum was added. Reheating the mixture to 190° C. led to gas evolution and the aluminum dissolved. The mixture was cooled to about 100° C., 40 ml (0.45 mole) of methyl disulfide was added and this mixture was then refluxed for 3 days.

VPC analysis showed 48 area % of methyl disulfide, 14 area % of 4-tert-butylphenol, 35 area % of 4-tert-butyl-2-(methylthio)phenol, and 2.8 area % of 4-tert-butyl-2,6-bis(methylthio)phenol. Ten additional ml (0.11 mole) of methyl disulfide was added to the mixture and refluxing was continued.

After a total of nine days of refluxing the mixture was stripped of excess methyl disulfide, dissolved in diethyl ether and extracted with 2N HCl. The ether layer was then washed with saturated NaCl and dried over MgSO4. Concentration and distillation gave, after a small forecut, 33.7 g (70% yield) of a product with a b.p. of 130°–131° C./0.3 mm. NMR analysis showed the product to be 4-tert-butyl-2,6-bis(methylthio)phenol.

EXAMPLE 3

Preparation of 4-Phenyl-2,6-bis(methylthio)phenol

Triethylaluminum, 1.7 ml (0.012 mole), was very carefully added dropwise to 34.0 g (0.20 mole) of 4-phenylphenol. The mixture was heated to 170° C., cooled to room temperature and 40 ml (0.45 mole) of methyl disulfide was added. This mixture was refluxed for 24 hours. Then 10 ml (0.11 mole) more of methyl disulfide was added and the refluxing was continued.

After a total of seven days of refluxing the mixture was cooled, stripped of excess methyl disulfide and diluted with 2N HCl. The mixture was then extracted with a CH2Cl2/THF solution and the organic phase was stripped of solvent leaving a black oil. Simple distillation gave 21.3 g of a product with a b.p. of 190°–207° C./1.0 mm. This product was recrystallized from CHCl3/heptane giving 19.3 g (37% yield) of a pale yellow solid having a m.p. of 87°–88° C. Analysis by NMR showed the product to be 4-phenyl-2,6-bis(methylthio)phenol.

EXAMPLE 4

Preparation of 2,4,6-Tris(methylthio)phenol

Phenol, 14.1 g (0.15 mole), was reacted with 0.30 g (0.011 mole) of aluminum (8–10 mesh) at 160°–180° C. until all the aluminum dissolved. The mixture was cooled, 60 ml (0.67 mole) of methyl disulfide was added and this mixture was refluxed for six days. The results of VPC analysis of samples taken after 4 days and after 6 days of refluxing are given in Table I.

TABLE I

| VPC Analysis Results for Example 4 | | |
|---|---|---|
| | Normalized Area % | |
| Compound | 4 days | 6 days |
| 2-(methylthio)phenol | 3.8 | 0.25 |
| 2,4-bis(methylthio)phenol | 13 | <1 |
| 2,6-bis(methylthio)phenol | 38 | 39 |
| 2,4,6-tris(methylthio)phenol | 44 | 60 |

The reaction mixture was diluted with diethyl ether, extracted with 6N HCl, washed with saturated NaCl and dried over $Na_2SO_4$. Distillation of the mixture gave 5.8 g (21% yield) of 2,6-bis(methylthio)phenol having a b.p. of 108°–113° C./0.15 mm and 13.9 g (40% yield) of 2,4,6-tris(methylthio)phenol having a b.p. of 147°–151° C./0.15 mm. The identity of each was confirmed by NMR analysis.

EXAMPLE 5

Reaction of Nonylphenol with Methyl Disulfide

A mixture of 39.6 g (0.18 mole) of Eastman practical grade nonylphenol (about a 1:1 ratio of the o-/p-isomers as shown by NMR) and 0.34 g (0.013 mole) aluminum was heated up to 260° C. No reaction was observed to occur and therefore the mixture was cooled and a few drops of triethylaluminum was added. The mixture was reheated to 180° C. which resulted in the aluminum reacting. Methyl disulfide, 20 ml (0.22 mole) was added at 100° C. and the mixture was refluxed for 36 hours. Ten ml (0.11 mole) more of methyl disulfide was added and refluxing was continued.

After refluxing one more day, 20 ml (0.22 mole) more of methyl disulfide was added to the reaction mixture and refluxing was continued an additional 3 days. The reaction mixture was cooled, diluted with THF/pentane, extracted with 6N HCl then with saturated NaCl and dried over $Na_2SO_4$.

Distillation gave a center cut fraction of 32.0 g (57% yield) having a b.p. of 150°–152° C./0.2 mm.

$^1H$ and $^{13}C$ NMR indicated this was a mixture of 4-nonyl-2,6-bis(methylthio)phenol and 6-nonyl-2,4-bis(methylthio)phenol.

EXAMPLE 6

Reaction of Phenol with Ethyl Disulfide

Phenol, 10.0 g (0.106 mole), and 0.21 g (7.8 mmole) of aluminum were heated in a 170° C. oil bath until all gas evolution ceased and all the aluminum dissolved. The mixture was cooled and 33 ml (0.27 mole) of ethyl disulfide was added. This mixture was heated to reflux.

After 16 hours Sample (A) was withdrawn and analyzed by VPC. After 23 hours Sample (B) was taken and after 41 hours Sample (C) was taken.

The reaction mixture was then stripped of excess ethyl disulfide, taken up in THF/diethyl ether, extracted with 6N HCl and then with saturated NaCl.

Distillation of the mixture yielded four fractions which are described in Table II. Compound identification was confirmed by NMR analysis.

TABLE II

| Distillation results of the Mixture of Example 6 | | |
|---|---|---|
| Fraction | b.p. | Major Component |
| (D) | 60–100/0.1 mm | — |
| (E) | 100–101/0.1 mm | Mixture of 2,4- and 2,6-bis(ethylthio)phenol |
| (F) | 101–146/0.1 mm | 2,6-bis(ethylthio)phenol |

TABLE II-continued

| Distillation results of the Mixture of Example 6 | | |
|---|---|---|
| Fraction | b.p. | Major Component |
| (G) | 146–154/0.1 mm | 2,4,6-tris(ethylthio)phenol |

The results of VPC analysis of the samples and fractions are given in Table III.

TABLE III

| VPC Analysis of Samples and Fractions of Example 6 | | | | | | | |
|---|---|---|---|---|---|---|---|
| | Area % | | | | | | |
| Compound | (A) | (B) | (C) | (D) | (E) | (F) | (G) |
| Ethyl disulfide | 58.5 | 52.1 | 39.3 | — | — | — | — |
| Phenol | 4.7 | 1.4 | 0.6 | — | — | — | — |
| 2-(ethylthio)phenol | 22.7 | 24.2 | 17.4 | 4.5 | — | — | — |
| 4-(ethylthio)phenol | 5.1 | 2.8 | 1.1 | 10 | 3.1 | — | — |
| 2,4-bis(ethylthio)phenol | 6.9 | 11.3 | 13.1 | 40 | 43.7 | 22 | — |
| 2,6-bis(ethylthio)phenol | 2.0 | 5.9 | 18.0 | 39 | 52.8 | 63 | — |
| 2,4,6-tris(ethylthio)phenol | 0.1 | 1.5 | 7.7 | — | — | 11 | 86 |

EXAMPLE 7

Reaction of 4,4'-Isopropylidenediphenol(Bisphenol A) with Methyl Disulfide

Bisphenol A, 45.6 g (0.20 mole), was dissolved in 20 ml of xylene at 150° C., cooled to about 100° C. and then cautiously treated with 2.7 ml (0.020 mole) of triethylaluminum. This mixture was reheated to 160° C., cooled to 120° C. and then 100 ml (1.11 mole) of methyl disulfide was added.

After 7 days at reflux the mixture, which was black in color, was cooled, poured onto cold dilute HCl and extracted with diethyl ether. The organic phase was washed with cold dilute NaCl and dried over $Na_2SO_4$. Removal of the solvent left a black oil which could not be crystallized from toluene/pentane.

The oil was dissolved in diethyl ether and extracted with dilute aqueous sodium hydroxide. The aqueous extract was acidified with HCl, extracted with diethyl ether and the etheral extract was dried ($Na_2SO_4$), filtered and the solvent removed to give a black oil. The oil was concentrated by distillation, dissolved in $CH_2Cl_2$ and passed through a column of silica gel. Removal of the solvent gave a dark yellowish brown oil which was distilled to give a viscous yellow oil having a b.p. of 224°–255° C./0.2–0.3 mm. VPC analysis showed the yellow oil to contain 31 area % of 2,2',6-tris(methylthio)-4,4'-isopropylidenediphenol and 60 area % of 2,2',6,6'-tetra(methylthio)-4,4'-isopropylidenediphenol. NMR and gc/ms analysis confirmed the identity of the compounds.

EXAMPLE 8

Preparation of 3,5-Dimethyl-2,4,6-tris(methylthio)phenol

A mixture of 12.2 g (0.1 mole) of Eastman 3,5-dimethylphenol and 0.16 g (0.006 mole) of aluminum was heated in a 170° C. oil bath. Vigorous gas evolution was observed. After 20–30 minutes no further reaction was observed. The mixture was cooled, 36 ml (0.4 mole) of methyl disulfide was added and the mixture was refluxed for 20 days.

The reaction mixture was cooled and stirred five minutes with 10 ml 1N HCl. The reaction mixture was observed to thicken and then thin. This mixture was then diluted with 20 ml diethyl ether, separated and the aqueous fraction was extracted three times with 20 ml portions of diethyl ether. The organic fractions were combined and the solvent was removed on a rotary evaporator. The dark liquid obtained was distilled through a 6" jacketed Vigreux column at full (0.3 mm) vacuum. Table IV gives the GC analysis results.

TABLE IV

GC Analysis of the Distillation Fractions of Example 8

| Fraction | Weight (g) | b.p.°C. | Normalized Area % | | | |
|---|---|---|---|---|---|---|
| | | | $2^a$ | $4^b$ | $bis^c$ | $tris^d$ |
| 1 | 1.43 | 83–96 | 90.7 | 0.1 | 0.9,7.5 | — |
| 2 | 7.34 | 124–130$^e$ | 0.5 | — | 99.3 | 0.2 |
| 3 | 6.71 | 130–136$^e$ | — | — | 93.1 | 6.5 |
| 4 | 2.57 | 127–153$^f$ | — | — | 30.4 | 69.6 |

$^a$3,5-dimethyl-2-(methylthio)phenol
$^b$3,5-dimethyl-4-(methylthio)phenol
$^c$3,5-dimethyl-2,4-bis(methylthio)phenol and 3,5-dimethyl-2,6-bis(methylthio)phenol
$^d$3,5-dimethyl-2,4,6-tris(methylthio)phenol
$^e$mainly at 129–130° C.
$^f$mainly at 143° C.

NMR shows fraction 2 to be a mixture of about 90:10 of 3,5-dimethyl-2,6-bis(methylthio)phenol and 2,4-bis(methylthio)phenol.

Fraction 4 was a yellow liquid that partially crystallized and formed white solid needles having a m.p. of 55°–57° C. upon being recrystallized twice from n-hexane. NMR analysis showed the needles to be pure 3,5-dimethyl-2,4,6-tris(methylthio)phenol.

EXAMPLE 9

Preparation of 4-(1,1,3,3-Tetramethylbutyl)2,6-bis(methylthio)phenol

Triethylaluminum, 0.3 ml (0.002 mole), was added to a mixture of 30.9 g (0.15 mole) of 4-(1,1,3,3-tetramethylbutyl)phenol (Schenectady Chemicals Inc., high purity grade, m.p. of 75°–88° C.) and 0.31 g (0.011 mole) of aluminum (8–10 mesh). This mixture was heated at 185°–190° C. until all of the aluminum dissolved (about one hour). The mixture was cooled and then 40 ml (0.45 mole) of methyl disulfide was added, and this mixture was heated to reflux.

After six days of reflux the mixture was cooled, poured into 100 ml of 3N HCl and extracted with diethyl ether/pentane. The organic layer was extracted with saturated NaCl and dried over $Na_2SO_4$. Distillation gave a forecut having a b.p. of 100°–137° C./0.1 mm and 27.7 g (62% yield) of a fraction having a b.p. of 137°–141° C./0.1 mm. NMR showed the fraction to be 4-(1,1,3,3-tetramethylbutyl)-2,6-bis(methylthio)phenol.

EXAMPLE 10

Reaction of Methyl Disulfide with 2,6-Dimethylphenol

A mixture of 20 g (0.164 mole) of 2,6-dimethylphenol and 0.31 g (0.011 mole) of 5–10 mesh aluminum was heated at 190° C. for 2 hr during which time the metal dissolved to give a red solution. The solution was cooled to 100° C. and 20 ml (0.22 mole) of methyl disulfide was added. The reaction was refluxed for 2 hr, cooled, an additional 10 ml (0.11 mole) of methyl disulfide was added, and the mixture refluxed overnight. The reaction was cooled, 17 ml (0.19 mole) of methyl disulfide was added, and the reaction refluxed for 24 hr. The reaction was again cooled, 15 ml (0.17 mole) of methyl disulfide was added, and the reaction refluxed for 3 more days.

At the end of the time, the reaction was cooled, stirred with a mixture of 50 ml 1.5N HCl and 100 ml of diethyl ether, and filtered. The greenish-brown solids were rinsed with 50 ml of diethyl ether. The filtrate and wash were combined, the aqueous phase separated, and the aqueous phase extracted once with 50 ml of diethyl ether. The combined organic phases were extracted with 25 ml water, dried ($Na_2SO_4$), filtered and the solvent removed to give 34 g of a reddish-black liquid.

VPC analysis showed 57 area % 2,6-dimethyl-(methylthio)phenol, 29 area % 2,6-dimethyl-bis(methylthio)phenol and 11 area % 2,6-dimethyl-bis(methylthio)phenol.

Distillation through a 7 cm jacketed Vigreux column gave 9.1 g (33% yield) of a slightly yellow liquid (b.p. 127°–130° C. at 3 mm) which crystallized upon standing. Nmr analysis indicated that the distillate was a 74:36 mixture of 2,6-dimethyl-4(methylthio)phenol and 2,6-dimethyl-3(methylthio)phenol.

Continued distillation gave 7.4 g (20% yield) of a yellow liquid (b.p. 159°–162° C./2 mm) which solidified upon standing. Combined VPC and nmr analysis showed that this fraction of the distillation was a 74:23 mixture of 2,6-dimethyl-3,4-bis(methylthio)phenol and 2,6-dimethyl-3,5-bis(methylthio)phenol.

Recrystallization of the solid from n-hexane and then $CCl_4$ gave pure 2,6-dimethyl-3,4-bis(methylthio)phenol as white crystals, m.p. 98°–100° C.

Use

The use of the compounds of this invention as antioxidants is yet another aspect of this invention.

In order to demonstrate the effectiveness of the compounds of this invention as antioxidants, a variety of these novel compounds were blended with lubricating oil and the resultant blends subjected to a bench test which measures the extent of oxidative decomposition and bearing corrosion experienced at elevated temperatures in the presence of a typical oxidation catalyst.

In particular, the antioxidant properties were tested by blowing air at the rate of 0.2 liters/min. through a base oil, Texaco Ursa P-20, 100 g, at 160° C. for 18 hours to which had been added enough iron naphthenate (a soluble oxidation catalyst) to provide 0.005% by weight iron. A half shell Cu/Pb engine bearing was also present in the oil during the test. The results of these tests are given in Table V. Additives (2) to (9) are compounds of this invention. Additive (10) is a commercially available antioxidant from Ethyl Corporation. The results show the viscosity increase in percent and the bearing weight loss (B.W.L.) in mg.

TABLE V

Bench Oxidation - Corrosion Test Results

| Additive | % by Wt. | Viscosity Increase % | B.W.L. (mg.) |
|---|---|---|---|
| (1) None | — | 829 | 91 |
| (2) A mixture of 4-nonyl-2,6-bis(methylthio)phenol and 6-nonyl-2,4-bis(methylthio)phenol | 1.0 | 69 | 97 |
| (3) 4-tert-butyl-2,6-bis(methylthio)phenol | 1.0 | 70 | 107 |
| (4) 4-phenyl-2,6-bis(methylthio)phenol | 1.0 | 56 | 14 |
| (5) 4-methyl-2,6-bis(methylthio)phenol | 1.0 | 6 | 20 |
| (6) 2,4,6-tris(methylthio)phenol | 1.0 | −2 | 6 |
| (7) 2,6-bis(methylthio)phenol | 1.0 | 17 | 9 |
| (8) 4-phenyl-2,6-bis(methylthio)phenol | 0.5 | 105 | 56 |
| (9) 4-methyl-2,6-bis(methylthio)phenol | 0.5 | 12 | 15 |

TABLE V-continued
Bench Oxidation - Corrosion Test Results

| Additive | % by Wt. | Viscosity Increase % | B.W.L. (mg.) |
| --- | --- | --- | --- |
| (10) 4,4'-methylenebis(2,6-di-tert-butylphenol)* | 1.0 | 68 | 111 |

*An antioxidant commercially available from Ethyl Corporation under the product designation ETHYL ® 702 Antioxidant.

Results of a sludge rating for (1)–(5) of Table I were D and the rating for (10) was C. A Sludge rating is a subjective determination of the amount of residue left on the sides of the test tubes after the Bench Oxidation-Corrosion Test is run. The ratings are as follows: A=-Clean, B=Very Light, C=Light, D=Heavy and E=Very Heavy.

The results shown in Table V demonstrate the effectiveness of a number of compounds of this invention as antioxidants.

Another series of tests was carried out following the above procedure. The results of these tests are given in Table VI.

TABLE VI
Bench Oxidation - Corrosion Test Results

| Additive | % by Wt. | Viscosity Increase % | B.W.L. (mg.) |
| --- | --- | --- | --- |
| (1) None | 1.0 | 619 | 132 |
| (2) 4-phenyl-2,6-bis(methylthio)phenol | 1.0 | 9 | 10 |
| (3) 4-tert-butyl-2,6-bis(methylthio)phenol | 1.0 | 53 | 64 |
| (4) A mixture of 3,5-dimethyl-2,6-bis(methylthio)phenol and 3,5-dimethyl-2,4-bis(methylthio)phenol* | 1.0 | 75 | 82 |
| (5) A mixture of 2,2',6,6'-tetra-(methylthio)-4,4'-isopropylidenediphenol** | 1.0 | 16 | −3 |
| (6) A mixture of 2,6-dimethyl-3,4-bis(methylthio)phenol and 2,6-dimethyl-3,5-bis(methylthio)phenol*** | 1.0 | 45 | 83 |

*About 90% by wt. of the 2,6-bis isomer and about 10% by wt. of the 2,4-bis isomer.
**About 60% by wt. of the 2,2'6,6'-tetra isomer and about 35% by wt. of the 2,2',6-tris isomer.
***About 74% by wt. of the 3,4-bis isomer and about 23% by wt. of the 3,5-bis isomer.

In the tests of Table VI the oil without any additive had a Sludge rating of E+ whereas additives (2)–(6) had sludge ratings of E.

The results in Table VI once again show that the compounds of this invention are effective as antioxidants.

From the results of these tests it can be seen that the compounds of this invention will exhibit antioxidant properties in a variety of substrates when used with the substrate in small concentrations, usually concentrations below about 2% by weight of the substrate, preferably within the range of from about 0.1% by weight to about 1% by weight and more preferably within the range of from about 0.25% by weight to about 0.75% by weight, typically about 0.5% by weight. As is well understood in the art, the particular concentration of an antioxidant employed will be governed to some extent by the nature of the substrate and the type and severity of the storage and service conditions to which the substrate will be exposed. Thus when using the compounds of this invention as antioxidants, the amounts may be varied to suit the needs of the occasion.

The substrates that may be protected by means of the antioxidant compounds of this invention include a broad range of organic materials of the type normally subject to oxidative deterioration in the presence of oxygen during storage or use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding agents nor flame suppressing additives and the degradation protected against is not combustion but, rather, the gradual deterioration of the organic composition due to the effects of oxygen over an extended period of time.

Examples of organic materials in which the additives, i.e. the products of this invention may be useful include homopolymers and copolymers of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additives may provide both antioxidant and antiozonate protection in natural and synthetic rubbers such as copolymers of olefinically unsaturated monomers including styrene-butadiene rubber (SBR rubber), ethylene-propylene copolymers, ethylene-propylene-diene terpolymers such as the terpolymer of ethylene, propylene and cyclopentadiene or cyclooctadiene. Polybutadiene rubbers such as cis-polybutadiene rubber may be protected. Poly-2-chloro-1,3-butadiene (neoprene) and poly-2-methyl-1,3-butadiene (isoprene rubber) may be stabilized by the present additives. Likewise, acrylonitrile-butadiene-styrene resins and polystyrenes (both crystal grades and rubber modified grades) are effectively stabilized. Ethylene-vinyl acetate copolymers may be protected, as are butene-methylacrylate copolymers. Nitrogen-containing polymers such as polyurethanes, nitrile rubber, and lauryl acrylate-vinylpyrrolidone copolymers may be effectively stabilized. Adhesive compositions such as solutions of polychloroprene (neoprene) in toluene may be protected.

Petroleum oils and waxes such as solvent-refined midcontinent lubricating oil, microcrystalline wax, and Gulf-coast lubricating oils are effectively stabilized. The additives may be useful in foamed plastics such as expanded polystyrene, polyurethane foams, and the various foamed rubbers, alkyd resins such as short oil terephthalic acid-glycerol-linseed oil resins, and resins including epoxide-modified alkyl resins. Epoxy resins themselves such as isopropylidenebisphenol-epichlorohydrin epoxy resins may be stabilized against degradation.

Hydrocarbons such as gasoline, kerosene, diesel fuel, fuel oil, furnace oil, and jet fuel may be effectively protected. Likewise, synthetic hydrocarbon lubricants, for example, α-decene trimer, polybutene lubricants, di- and tri-$C_{12-30}$ alkylated benzene and naphthalene synthetic lubricants are likewise protected.

Organometallics such as tetraethyllead, tetramethyllead, tetravinyllead, ferrocene, methyl ferrocene, cyclopentadienyl magnesium tricarbonyl, methyl cyclopentadienyl magnesium tricarbonyl, cyclopentadienyl nickel nitrosyl, and the like, may be effectively protected against oxidative degradation. Silicone oils and greases may be also protected.

Synthetic ester lubricants such as those used in turbines and turbojet engines may be given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions mixtures of polyols, polycarboxylic acids, and aliphatic monocarboxylic acids and/or monohydric alkanols. An example of these complex esters is the condensation product formed from adipic acid, ethylene glycol and a mixture of $C_{5-9}$ aliphatic monocarboxylic acids. Plasticizers such as dioctyl phthalate may be effectively protected. Heavy petroleum fractions such as tar and asphalt may also be protected should the need arise.

Polyamides such as adipic acid-1,6-diaminohexane condensates and poly-6-aminohexanoic acid (nylon) may be effectively stabilized. Polyalkylene oxides such as copolymers of phenol with ethylene oxide or propylene oxide may be stabilized. Polyphenylene ethers such as poly-2,6-dimethylphenylene ether formed by polymerization of 2,6-dimethylphenol using a copper-pyridine or like catalyst may be stabilized. Polycarbonate plastics and polyformaldehyde resins may be also protected.

Linear polyesters such as phthalic anhydride-glycol condensates may be given a high degree of protection. Other polyesters such as trimellitic acid-glycerol condensates may be also protected. Polyacrylates such as polymethlacrylate and polymethylmethacrylate may be effectively stabilized. Polyacrylonitriles and copolymers of acrylonitriles with other olefinically unsaturated monomers such as methylmethacrylates may be also effectively stabilized.

The additives may be used to protect any of the many organic substrates to which an antioxidant is normally added. It may be used where economics permit to protect such substrates as asphalt, fluorocarbons such as Teflon, polyvinyl acetate, polyvinylidene chloride, coumarone-indene resins, polyvinyl ethers, polyvinylidene bromide, polyvinylbromide, acrylonitrile, vinyl bromide copolymer, vinyl butyral resins, silicones such as dimethylsilicone lubricants, phosphate lubricants such as tricresylphosphate, and the like.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

Other utilities for the compounds of this invention include their use as raw materials in the synthesis of polymers and as intermediates in the synthesis of pharmaceuticals, pesticides, herbicides, and the like.

What is claimed is:

1. A process for the preparation of substituted phenols which comprises reacting a phenol having at least two positions available for substitution on a phenolic ring with an excess of a hydrocarbyl disulfide in the presence of an aluminum phenoxide catalyst so that (hydrocarbylthio)phenol is prepared containing at least two hydrocarbylthio groups on a phenolic ring, the molar ratio of said catalyst relative to said disulfide being between about 0.002 and 0.3.

2. A process of claim 1 wherein said process is carried out at a temperature of from between about 100° to about 300° C.

3. A process of claim 1 wherein said molar ratio is between about 0.01 and 0.1.

4. A process of claim 1 wherein the said phenol and said hydrocarbyl disulfide are employed in a molar ratio of about 1:2.1 to about 1:20.

5. A process of claim 1 wherein the hydrocarbylthiol formed as by-product in the reaction is removed from the reaction vessel essentially as rapidly as it is formed.

6. A process of claim 1 wherein said hydrocarbyl disulfide is an alkyl disulfide.

7. A process of claim 6 wherein said disulfide is methyl disulfide or ethyl disulfide.

8. A process of claim 1 wherein said aluminum phenoxide is formed in situ by reacting aluminum with said phenol.

9. A process of claim 1 wherein said phenol and said hydrocarbyl disulfide are employed in a molar ratio of about 1:2.1 to about 1:20, wherein said disulfide is a lower alkyl disulfide, wherein the lower alkyl mercaptan by-product of the reaction is removed from the reaction mixture during the course of the reaction, and wherein the reaction is performed at a temperature within the range of from about 100° to about 200° C.

10. A process of claim 1 wherein the reaction is conducted at reflux at a temperature within the range of from about 100° to about 200° C. and wherein said disulfide is methyl disulfide or ethyl disulfide.

11. A process of claim 1 wherein said phenol is a compound having the formula

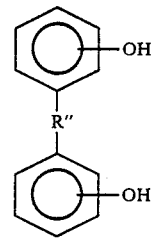

wherein R″ is an alkylidene group or alkylene group containing up to 4 carbon atoms, a direct carbon-to-carbon bond linking the two phenolic rings together, or an oxygen atom, and said disulfide is a lower alkyl disulfide.

12. A process of claim 11 wherein the hydroxyl groups of said phenol are in the 4 and 4' positions relative to R''.

13. A process of claim 12 wherein said phenol is 4,4'-isopropylidenediphenol.

14. A process of claim 12 wherein said phenol is 4,4'-isopropylidenediphenol and said disulfide is methyl disulfide.

15. A process of claim 1 wherein said phenol is a compound having the formula

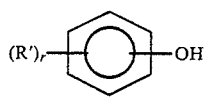

wherein r is an integer from zero to 1 (both inclusive) and R' is a hydrocarbyl group essentially devoid of olefinic and acetylenic unsaturation and containing up to about 50 carbon atoms.

16. A process of claim 1 wherein said phenol is a compound having the formula

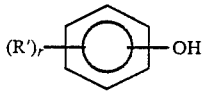

wherein r is one and R' is a long chain alkyl group having from about 50 to about 700 or more carbon atoms.

17. A process of claim 1 wherein said phenol is a compound having the formula

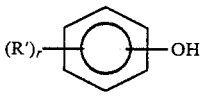

wherein r is 2 and each R' is a hydrocarbyl group essentially devoid of olefinic and acetylenic unsaturation and containing up to about 30 carbon atoms.

18. A compound corresponding to the formula:

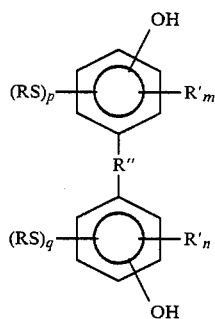

wherein R is a hydrocarbyl group containing up to about 10 carbons; the R' substituents are independently selected from hydrogen and hydrocarbyl groups; R'' is an alkylidene or alkylene group containing about 1–10 carbons; m, n, p, and q have values of 0–4, at least one of p and q being an integer of at least 2, and the total of m and p being 4 and the total of n and q being 4; said hydrocarbyl groups being essentially devoid of olefinic and acetylenic unsaturation.

19. A compound of claim 18 wherein the hydroxyl groups of said compound are in the 4 and 4' positions relative to R''.

20. A compound of claim 19, namely 2,2',6,6'-tetra(-methylthio)-4,4'-isopropylidenediphenol.

21. A mixture of 2,2',6,6'-tetra(methylthio)-4,4'-isopropylidenediphenol and 2,2',6-tris(methylthio)-4,4'-isopropylidenediphenol.

22. A compound corresponding to the formula:

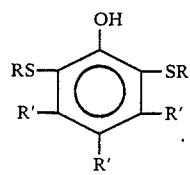

wherein R is a hydrocarbyl group containing up to about 10 carbons, at least two of the R' substituents are the same or different hydrocarbyl groups, and the remaining R' is hydrogen or a hydrocarbyl group, said hydrocarbyl groups being essentially devoid of olefinic and acetylenic unsaturation.

23. A compound corresponding to the formula:

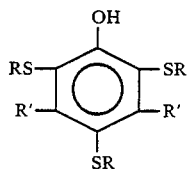

wherein R is a hydrocarbyl group containing up to about 10 carbons and the R' substituents are independently selected from hydrogen and hydrocarbyl groups, said hydrocarbyl groups being essentially devoid of olefinic and acetylenic unsaturation.

24. A compound corresponding to the formula:

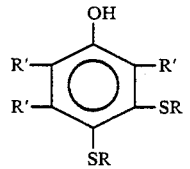

wherein R is a hydrocarbyl group containing up to about 10 carbons, the R' substituents in the 2- and 6-positions are the same or different hydrocarbyl groups, and the remaining R' is hydrogen or a hydrocarbyl group, said hydrocarbyl groups being essentially devoid of olefinic and acetylenic unsaturation.

* * * * *